(12) United States Patent
Wong et al.

(10) Patent No.: US 9,023,898 B2
(45) Date of Patent: May 5, 2015

(54) FLUSHING SOLUTION

(75) Inventors: David Wong, Merseyside (GB);
Christian Lingenfelder, Ulm (DE)

(73) Assignee: Fluoron GmbH, Neu-Ulm (DE)

( * ) Notice: Subject to any disclaimer, the term of this patent is extended or adjusted under 35 U.S.C. 154(b) by 817 days.

(21) Appl. No.: 12/743,697

(22) PCT Filed: Nov. 19, 2008

(86) PCT No.: PCT/EP2008/009769
§ 371 (c)(1),
(2), (4) Date: May 19, 2010

(87) PCT Pub. No.: WO2009/065565
PCT Pub. Date: May 28, 2009

(65) Prior Publication Data
US 2010/0274215 A1    Oct. 28, 2010

(30) Foreign Application Priority Data
Nov. 19, 2007  (DE) .......................... 10 2007 055 046

(51) Int. Cl.
*A61K 47/30* (2006.01)
*A61K 9/00* (2006.01)
*A61K 47/06* (2006.01)

(52) U.S. Cl.
CPC ............... *A61K 9/0048* (2013.01); *A61K 47/06* (2013.01); *Y10S 514/912* (2013.01)

(58) Field of Classification Search
USPC .......................................... 514/1, 772.3, 912
See application file for complete search history.

(56) References Cited

U.S. PATENT DOCUMENTS

| | | | |
|---|---|---|---|
| 4,819,617 A * | 4/1989 | Goldberg et al. ............. | 128/897 |
| 5,219,844 A | 6/1993 | Peyman et al. | |
| 5,336,487 A | 8/1994 | Refojo et al. | |
| 5,972,909 A * | 10/1999 | Di Napoli ...................... | 514/54 |
| 6,262,126 B1 | 7/2001 | Meinert | |
| 6,290,690 B1 * | 9/2001 | Huculak et al. ............... | 604/521 |
| 6,902,737 B2 * | 6/2005 | Quemin ........................ | 424/401 |
| 7,244,240 B2 | 7/2007 | Nazarifar et al. | |
| 2006/0177524 A1 | 8/2006 | Armitage et al. | |

FOREIGN PATENT DOCUMENTS

| | | |
|---|---|---|
| DE | 102005017279 A1 | 10/2006 |
| RU | 2192228 C1 * | 11/2002 |
| WO | WO03079927 A2 | 10/2003 |

OTHER PUBLICATIONS

Ishikawa et al., Effect of non-Newtonian property of blood on flow through a stenosed tube, 1998, Fluid Dyn. Res., vol. 22, Issue 5, printed from http://iopscience.iop.org/1873-7005/22/5/A01, Abstract only, 1 page.*
Lecture on Annual Meeting of Korean Society of Anesthesiologists, Fujita, Journal of th eKorean Society of Anesthesiologists, vol. 16, No. 2,1983, 71-72.*
BSS (Balance Salt Solution), South African Electronic Package Inserts, Mar. 16, 2004, printed from http://web.archive.org/web/20040316193924/http://home.intekom.com/pharm/alcon/bss.html, 2 pages.*
Kataoka et al., Viscosity—Molecular Weight Relationship for Polydimethylsiloxane, 1966, Journal of Polymer Science Part B: Polymer Letters vol. 4, Issue 5, 317-322.*
Translation of RU 2192228 C1, patent published on Nov. 10, 2002, translation by USPTO translation branch on May 3, 2012, 6 pages.*
Soheilian et al., "Experimental retinal tolerance to very low viscosity silicone oil (100 cs) as a vitreous substitute compared to higher viscosity silicone oil (5000 cs)," International Opthalmology 19:57-61, 1995.
International Search Report and Written Opinion of international application No. PCT/EP2008/009769, dated Apr. 29, 2009, 12 pp.
International Preliminary Report on Patentability from international application No. PCT/EP2008/009769, dated Jun. 1, 2010, 7 pp.
Translation of Russian patent No. 2192228 C1, by V N Kazajkin, dated Nov. 10, 2002.

* cited by examiner

*Primary Examiner* — Gigi Huang
(74) *Attorney, Agent, or Firm* — Shumaker & Sieffert, P.A.

(57) ABSTRACT

A flushing solution is described which is suitable for use in surgical, in particular ophthalmological, operations and which contains a non-Newtonian fluid. The use of such a flushing solution is also described. The flushing solution can be used as an intraoperative instrument, particularly as an instrument for manipulating intraocular structures such as retina.

12 Claims, No Drawings

FLUSHING SOLUTION

FIELD OF THE INVENTION

The invention relates to a non-Newtonian solution for use as a flushing solution for surgical operations, in particular in ophthalmology.

BACKGROUND OF THE INVENTION

During surgical operations it is often necessary to flush the surgical site during the operation in order to free it of undesirable material. Isotonic saline solution, optionally containing additives, is generally used for this purpose.

Many diseases of the eyes of vertebrates are attributable to changes in the retina or the vitreous body. The vitreous body is part of the eye and serves to maintain the specific shape of the eye. The vitreous body is disposed between the retina of the eye and the lens and consists of about 98% water and about 2% hyaluronic acid and a network of collagen fibres, which serve to stabilise the water owing to their retention capacity. The gelatinous consistency and transparency of the vitreous body are obtained as a result.

The possibilities of treating disorders of the eye, in particular of the retina, such as retinal detachment, have increased considerably in recent years. For the doctor carrying out such treatment, it is important to recognise the diseased or damaged areas correctly. A requirement for successful surgical operations in general and on the eye in particular is good visibility of the anatomical structures.

Part of such a treatment can be the surgical removal of the vitreous body (vitrectomy). In order to remove the vitreous body, three small incisions are made in the sclera of the eye, which extend into the posterior chamber of the eye, in which the vitreous body is located. Appropriate surgical instruments can then be introduced into the eye through the incisions. In order to cause as little damage as possible to the eye, the incisions should be very small. The surgical site is flushed during the operation, generally with saline solution.

In order that the eye does not lose its shape and suffer secondary damage owing to the loss of pressure that occurs when the vitreous body, which provides stability, is removed by suction, a fluid substitute is introduced into the cavity in place of the vitreous body and keeps the internal pressure constant. In the prior art, an isotonic saline solution is conventionally used as the flushing solution because of its chemical composition and its physical properties, because a saline solution is miscible with the water of the vitreous body in an optimum manner, so that the two fluids can be exchanged without problems.

During the treatment it is necessary to flush the site of the surgical operation. However, visibility of the surgical site must not be restricted thereby. In addition, the flushing solution must be physiologically acceptable, and it must be possible to introduce and remove it without difficulty.

It has now been found that isotonic saline solution, which is frequently used, has the disadvantage, on account of its good miscibility with water, that it mixes with the other fluids, such as aqueous fluid and blood, and thereby becomes coloured and cloudy. Such clouding leads to restricted visibility of the surgical site, which is extremely undesirable. Furthermore, glutathione and glucose are added as standard to the saline solution. Because such a solution is unstable, however, glutathione and glucose can only be added immediately prior to use, which is complex and increases the risk of contamination.

Although attempts have been made in the prior art to use a very wide variety of tamponade fluids, the only solutions usually mentioned for the flushing solutions used during the surgical operation are aqueous solutions, which preferably have approximately the density of water.

DE 60107451T2, for example, describes the use of a saline solution as a conventional ophthalmic fluid for flushing during a vitrectomy. After the vitrectomy, it is necessary to introduce a substance that (temporarily) replaces the vitreous body. In this connection, WO 03/079927 describes the use of perfluorinated alkanes as a substitute fluid and tamponade preparation in surgical operations, in particular on the retina. Such perfluorinated alkanes have the advantage that, owing to their high density, they accumulate in the lower portion of the vitreous body in particular and accordingly facilitate treatment of the retina for the surgeon. The high density is also a disadvantage, however, because the perfluorinated alkanes, on account of their high density, exert pressure on the tissues. A further disadvantage of perfluorinated alkanes is their above-average high price and, on the other hand, their extreme hydrophobicity and lipophobicity. Perfluorinated alkanes are scarcely soluble, either in hydrophilic or lipophilic or fluorophilic substances, which makes the removal of the preparation from inside the vitreous chamber considerably more difficult and gives rise to additional costs.

When using vitrectomes that operate with different cutting rates, a further problem can occur. When working very close to the retina, the retina can start to flutter, which makes it difficult for the surgeon to work with accuracy and puts the retina in danger.

Because of the disadvantages of the flushing solutions for surgical operations known hitherto, and in particular when they are used in ophthalmological operations, an improved preparation is desirable.

It was an object of the invention to provide a flushing solution which makes it easier for the surgeon to perform the surgical operation and thereby prevents secondary damage, which is readily available, which is physiologically acceptable and well tolerated, and which is markedly reduced in price as compared with the perfluorinated alkanes mentioned above. It was a further object of the invention to provide a flushing solution for surgical operations on the eye which is physiologically acceptable and easy to introduce but at the same time permits good visibility of the surgical site and facilitates the use of surgical devices, for example vitrectomes.

The object is achieved by a flushing solution for surgical, in particular ophthalmological, operations, in particular in vitreous body and retinal surgery, as defined in claim 1.

It has been found, surprisingly, that it is advantageous for surgical operations to use a non-Newtonian fluid, in particular a non-aqueous and water-immiscible non-Newtonian fluid, as the flushing solution, because such a flushing solution on the one hand does not mix with blood, thus preventing clouding and impairment of visibility, and on the other hand is able to dampen shear forces, which occur when surgical devices are used. This is generally advantageous in the case of surgical operations, especially when instruments whose shear forces have an adverse effect are being used.

The flushing solution according to the invention has the effect that there is no mixing with the fluids present at the surgical site, in particular blood, so that the doctor has a better overview. Moreover, fluttering or movement of tissue under the action of shear forces is prevented or reduced. The latter is particularly important in the case of sensitive tissues, such as the retina.

Fundamental to the present invention is the use of a non-Newtonian fluid for flushing during a surgical operation. Non-Newtonian fluids are defined as fluids in which the shear stress at constant temperature is not proportional to the velocity gradient, that is to say fluids which absorb and accordingly dampen the shear forces acting on them.

The flushing fluid used is additionally immiscible or scarcely miscible with water, in order to avoid mixing with blood and accordingly staining. Suitable physiologically acceptable fluids that are immiscible or scarcely miscible with water are known to the person skilled in the art. A fluid that is immiscible or scarcely miscible with water is understood as being a scarcely, sparingly or very sparingly water-soluble solvent, which is soluble in water only in an amount of less than 20 parts per 100 parts of water, preferably less than 10 parts, particularly preferably less than 5 parts.

For use in ophthalmology, it is necessary to distinguish between the vitreous body and the flushing solution during the operation, which permits the solution according to the invention. At the same time, the base of the vitreous body should be clearly discernible at all times, in order to facilitate the operation for the surgeon, in particular in order to avoid secondary damage by the surgical procedure.

Surprisingly, it has been found that silicone oils having a specific density and a specific viscosity are particularly suitable as a flushing solution for surgical, in particular ophthalmological, operations and are not only able to replace the expensive perfluorinated compounds but additionally provide further advantages.

Silicone oils have been known for a long time. They are used in many fields, for example in the industrial sector as antifoams or for coatings, but also in cosmetics, for example as glossing agents and agents that improve adhesion. In medical technology, they are known predominantly from plastic surgery.

By means of diverse syntheses they can be synthesised in any desired configuration according to the field of application. They include both cyclic and aliphatic silicones and in particular siloxanes, including polydimethylsiloxanes (PDMS). The range of aliphatic silicones and, in particular, siloxanes extends from low molecular weight to high molecular weight, the high molecular weight types including those having viscosities far in excess of 1 million mPas.

Processes for the preparation of silicone oils are known, and silicone oils are readily obtainable relatively inexpensively.

The inventors have now found, surprisingly, that specific silicone oils are highly suitable as a flushing solution for surgical, in particular ophthalmological, operations.

An important advantage of the non-Newtonian fluids, in particular silicones, used according to the invention is their poor miscibility with blood. The flushing solutions used hitherto mix with blood, which results in impaired visibility during the operation. With silicones, no mixing occurs; a phase boundary forms, which is readily visible to the doctor. In addition, the silicone oil can push the blood back, so that, under certain circumstances, there is even a certain haemostatic effect.

The lasting transparency of the non-Newtonian fluids, in particular silicones, used according to the invention, which is not impaired by blood or other aqueous solutions, has yet a further advantage. The solution according to the invention is preferably intended for use inter alia as a flushing solution in the case of vitrectomy. The vitrectomy is carried out in order to remove the vitreous body, which is necessary if the vitreous body is inflamed, if an operation is to be performed on the retina, or if the vitreous body has become opaque. In each case, the vitreous body must be so removed that the retina is not detached with it. The vitreous body is in contact with the retina via the vitreous body limiting membrane. If, therefore, the vitreous body is already cloudy, it is all the more important that the flushing solution is neither cloudy nor made cloudy by blood and other constituents.

An important property of the silicone oil used according to the invention is its density. Only those silicone oils that have a density less than that of water, that is to say less than 1.0 g/cm$^3$, are suitable. Preferably, silicone oils having a density in the range from 0.80 to 0.98 g/cm$^3$, particularly preferably from 0.90 to 0.98 g/cm$^3$, are used. Because their density is less than that of water, such silicone oils are capable of filling up even the upper region of the vitreous chamber. By infusion of the silicone oil preparation according to the invention, the subretinal fluid is displaced to the posterior region of the vitreous chamber. This brings considerable advantages, in particular in the case of operations in the anterior region of the vitreous chamber. In that case, the infusion solution according to the invention not only serves as a volume replacement for the vitreous body, but also acts as a stabiliser for the retina, preventing it from collapsing.

Another advantage of the flushing solution according to the invention can be attributed to its non-Newtonian properties. It has been found that the flushing solution according to the invention can dampen vibrations or fluttering of the retina, which occur when a vitrectome is used close to the retina. For this reason, the silicone oil also plays a part in making the operation more controllable and safer, and therefore easier, for the surgeon.

The second important property of the silicone oil according to the invention is its viscosity. Only when the viscosity is sufficiently low can the flushing solution according to the invention be supplied and removed via thin cannulas or needles. The viscosity must therefore not exceed a value of 100 mPas when measured at 25° C. and ambient pressure using a Schott CT52 UBBELOHDE capillary viscometer.

The silicone oils according to the invention having a viscosity of approximately from 0.1 to 100 mPas are distinguished over the perfluorinated alkanes used in the prior art by a markedly lower viscosity. It has been found that silicone oils having a viscosity in that range are easy to process. They can also readily be conveyed to the inside of the eye, and removed therefrom again, through thin cannulas, as are used in corresponding surgical operations. Up to 25-gauge cannulas are nowadays used in operations on the eye, and the fluid must flow through the very narrow lumen thereof. The flushing solution according to the invention can also be applied through such cannulas. Silicone oils that have a viscosity higher than 100 mPas are viscous and cannot be supplied and removed through such thin cannulas at all and to only a limited extent through thick cannulas. Although lower viscosity silicone oils, for example having a viscosity of 0.1 mPas, are extremely thin, their vapour pressure, and accordingly their volatility, is too high for them to be used expediently. Moreover, problems with sterilisability can occur with silicone oils having a viscosity below 0.1 mPas. Silicones having only 1 siloxane unit could be unsuitable for a solution for use in the eye for reasons of toxicity, which is not the case with those defined according to the invention. On the contrary, the silicone oils that come into consideration according to the invention are distinguished by their biocompatibility.

Silicone oils whose viscosity is approximately from 0.5 to 50 mPas, more preferably from 1 to 20 mPas, are therefore particularly suitable. A balanced relationship between volatility and viscosity is obtained in that range, so that such silicone oils can easily be introduced into the vitreous chamber through appropriate cannulas, and their volatility is sufficiently low that they remain in that chamber without evaporating through the other surgical incisions or via the cornea. Silicone oils whose viscosity is approximately from 2 to 10 mPas are particularly suitable. They have a considerably reduced volatility as compared with silicones having a viscosity of less than 2 mPas. The upper limit of 10 mPas indicates the value which permits optimum flow behaviour of the silicone oil and therefore the preparation of a particularly suitable infusion solution for ophthalmological operations.

According to the invention there are used as the silicone oil flowable silicones, in particular siloxanes, which satisfy both the required properties. Methylsiloxanes and their polymers and dimethylsiloxanes and their polymers are highly suitable. The silicones can be both unsubstituted and substituted. Substitution is understood as meaning the replacement of a hydrogen atom bonded to a silicon atom by a different atom or a molecular group. Common substituents are straight-chained, branched or cyclic alkyl groups having from 1 to 18 carbon atoms or aryl groups having from 6 to 15 carbon atoms. The alkyl or aryl groups can themselves be substituted. The substituents can be present in blocks or distributed over the siloxane chain, and the amount thereof can be adjusted in a known manner according to the desired properties.

There come into consideration according to the invention in particular unsubstituted as well as alkyl- and aryl-substituted silicone oils. Polydimethylsiloxanes (PDMS), which can be unsubstituted or substituted, are particularly suitable. In the case of substituted silicones, aryl-substituted products, and of those phenyl-substituted products, are readily available.

Silicone oils generally indicates immiscibility with water and therefore also with blood. As a result, after the preparation according to the invention has been introduced into the vitreous chamber of the eye, an interface forms at the phase boundary between the silicone oil and the vitreous body. The different refractive indices of silicone oil and water therefore have the advantage that the surgeon knows, at any time during the operation, where he is located with his surgical instrument, either in the vitreous body or in the silicone oil, and he is better able to judge whether the vitreous body has been removed completely. The formation of the interface helps the surgeon with orientation. From this point of view, therefore, silicone oils whose refractive index differs markedly from that of water are suitable. Of the substituted silicone oils, phenyl-substituted silicone oils, such as phenyl dimethicone, phenyl methicone, phenyl trimethicone, diphenyl dimethicone, diphenyl methicone, diphenyl trimethicone, are particularly advantageous in this respect, because phenyl groups increase the refractive index and, moreover, provide for increased transparency. The increased refractive index makes the difference between the refractive indices of water and silicone oil even greater, so that the interface of the two fluids is even more clearly apparent to the surgeon. This results in a considerable simplification of the complicated surgical operation and accordingly an improved outcome of the operation.

The silicone oils that are suitable for the flushing solution according to the invention include inter alia: n-polydimethylsiloxanes, iso-polydimethylsiloxanes, aryl-substituted PDMS, such as phenyl-polydimethylsiloxanes, diphenyl-polydimethylsiloxanes, polyphenyl-polydimethylsiloxanes, alkyl-substituted PDMS, such as methyl-polydimethylsiloxanes, ethyl-polydimethylsiloxanes, propyl-polydimethylsiloxanes and the like, PDMS having other substituents, such as fluoroalkyl-substituted PDMS. This list is intended to give examples of suitable silicone oils for use in a flushing solution according to the invention, without being limited thereto. Examples of suitable compounds are listed hereinbelow: bis-diphenylethyl disiloxane, bisphenyl hexamethicone, capryl dimethicone, caprylyl dimethicone, caprylyl methicone, dimethicone, disiloxanes, hexyl dimethicone, hexyl methicone, lauryl dimethicone, lauryl methicone, methicone, methyl trimethicone, phenylethyl dimethicone, phenylethyl disiloxane, phenylpropyl ethyl methicone, phenylpropyl trimethicone, phenyl trimethicone, trifluoropropyl dimethicone, trifluoropropyl methicone, trisiloxanes, etc.

In one embodiment, the flushing solution of the present invention comprises at least one fluid selected from silicone oil, polyhydric alcohols having 2 to 4 carbon atoms, polyethylene oxide-containing fluids and/or polypropylene oxide-containing fluids or mixtures thereof.

As stated above, silicone oils are used according to the invention in order to eliminate the disadvantages associated with the use of perfluorinated alkanes. The use of semi-fluorinated alkanes is also not preferred for similar reasons. However, because of the good miscibility of semi-fluorinated compounds and silicones, the addition of a small amount of semi-fluorinated compounds can be useful in some cases, for example in order specifically to adjust the density and/or viscosity. Depending on the substances used and on the intended purpose, up to 10 vol % semi-fluorinated alkanes can preferably be added. Suitable semi-fluorinated alkanes are described, for example, in EP0859751.

The addition of a semi-fluorinated alkane offers a further advantage. Semi-fluorinated alkanes have a higher dissolving power for active ingredients than do silicones. In a preferred embodiment, therefore, one or more semi-fluorinated alkanes can be added to the flushing solution according to the invention as solubilisers for active ingredients. There come into consideration as active ingredients in this connection medicaments, antioxidants, nutrients for the eye or the like. Soothing and antibiotic agents may be mentioned as examples of medicaments. Examples of antioxidants are compounds that capture free radicals. Sugars, such as glucose, may be mentioned as nutrients.

The amount of semi-fluorinated alkane(s) in the flushing solution, preferably in silicone, can vary in dependence on the desired properties. By means of the semi-fluorinated alkane it is possible not only to improve the solubility for specific agents, but also to adjust the density. Preferably, semi-fluorinated alkane is added in an amount of more than 1 wt. %, more preferably more than 5 wt. %. The amount of semi-fluorinated alkane can also be higher. The person skilled in the art can readily establish the appropriate ratio of silicone to semi-fluorinated alkane by means of a few routine experiments, a ratio of silicone to semi-fluorinate alkane in the range from 50:1 to 1:2 being particularly suitable.

The described silicone oils are suitable for the preparation of flushing solutions for ophthalmological operations, in particular also as an intraoperative instrument, in particular as an instrument for manipulating intraocular structures. The preparations according to the invention are advantageous in ophthalmological operations in particular for flushing the vitreous chamber. The preparations according to the invention are therefore preferably prepared in the form of a flushing solution which is used in operations on the eye, in particular in the region of the retina.

The invention claimed is:
1. A method of flushing a vitreous body or a retina comprising, when operating on the retina, flushing the vitreous body or the retina with a flushing solution and removing the flushing solution after flushing, wherein the flushing solution comprises a non-Newtonian fluid comprising a silicone oil, selected from a group consisting of a substituted polydimethylsiloxane, an unsubstituted polydimethylsiloxane, or mixtures thereof, and wherein the silicone oil has a density of less than 1 g/cm3 and a viscosity of from 0.1 mPa-s to 100 mPa-s.

2. The method of claim 1, further comprising locating an interface formed between the vitreous body and the flushing solution and removing the vitreous body.

3. The method of claim 1, wherein the silicone oil has a density from 0.80 g/cm$^3$ to 0.98 g/cm$^3$.

4. The method of claim 1, wherein the silicone oil has a viscosity from 0.5 mPa-s to 50 mPa-s.

5. The method of claim 1, wherein the silicone oil has a viscosity from 2 mPa-s to 10 mPa-s.

6. The method of claim 1, wherein the silicone oil is formed from siloxanes having from 2 siloxane units to 10 siloxane units.

7. The method of claim 1, wherein the silicone oil is phenyl-substituted.

8. The method of claim 1, wherein the flushing solution further comprises a semi-fluorinated alkane.

9. The method of claim 8, wherein the flushing solution having a density of less than 1 g/cm$^3$ comprises the silicone oil and the semi-fluorinated alkane.

10. The method of claim 8, wherein the flushing solution comprises the silicone oil and the semi-fluorinated alkane having a ratio of from 50:1 to 1:2.

11. The method of claim 1, wherein the flushing solution further comprises one or more water-insoluble active ingredients.

12. The method of claim 1, wherein the flushing solution further comprises at least one of medicaments, antioxidants and nutrients.

\* \* \* \* \*